(12) United States Patent
Li et al.

(10) Patent No.: US 12,331,067 B2
(45) Date of Patent: *Jun. 17, 2025

(54) METHOD FOR PREPARING $^{18}$F-BPA AND INTERMEDIATE

(71) Applicant: NEUBORON MEDTECH LTD., Jiangsu (CN)

(72) Inventors: Shi-hong Li, Jiangsu (CN); Jing He, Jiangsu (CN); Heng Yan, Jiangsu (CN); Fei Cai, Jiangsu (CN)

(73) Assignee: NEUBORON MEDTECH LTD., Jiangsu (CN)

( * ) Notice: Subject to any disclaimer, the term of this patent is extended or adjusted under 35 U.S.C. 154(b) by 0 days.

This patent is subject to a terminal disclaimer.

(21) Appl. No.: 18/132,479

(22) Filed: Apr. 10, 2023

(65) Prior Publication Data

US 2023/0242555 A1 Aug. 3, 2023

Related U.S. Application Data

(63) Continuation of application No. 17/171,224, filed on Feb. 9, 2021, now Pat. No. 11,655,261, which is a
(Continued)

(30) Foreign Application Priority Data

| Aug. 17, 2018 | (CN) | 201810940708.3 |
| Dec. 5, 2018 | (CN) | 201811478614.5 |
| Dec. 5, 2018 | (CN) | 201811478615.X |

(51) Int. Cl.
C07C 229/34 (2006.01)
C07B 59/00 (2006.01)
(Continued)

(52) U.S. Cl.
CPC ............ *C07F 5/027* (2013.01); *C07B 59/004* (2013.01); *C07C 229/34* (2013.01); *C07C 249/02* (2013.01)

(58) Field of Classification Search
CPC ..... C07F 5/027; C07B 59/004; C07C 229/34; C07C 249/02
See application file for complete search history.

(56) References Cited

U.S. PATENT DOCUMENTS

| 5,935,944 A | 8/1999 | LaHann |
| 11,655,261 B2 * | 5/2023 | Li ............................ C07F 5/025 |
| | | 558/298 |

(Continued)

FOREIGN PATENT DOCUMENTS

| CN | 102887913 B | 2/2015 |
| CN | 105916836 A | 8/2016 |

(Continued)

OTHER PUBLICATIONS

CN 2020-10505139, priority document for WO 2021244529 A1 filed Jun. 5, 2020. (Year: 2020).*

(Continued)

*Primary Examiner* — Joseph K McKane
*Assistant Examiner* — Ashli Ariana Chicks
(74) *Attorney, Agent, or Firm* — Troutman Pepper Locke LLP; Tim Tingkang Xia, Esq.

(57) ABSTRACT

A method for preparing $^{18}$F-BPA and an intermediate, by which high-purity $^{18}$F-BPA is obtained. The method simplifies the synthesis steps after $^{18}$F labeling, and is easy to operate and efficient.

20 Claims, 3 Drawing Sheets

Related U.S. Application Data continuation of application No. PCT/CN2019/100678, filed on Aug. 15, 2019.

(51) Int. Cl.
*C07C 249/02* (2006.01)
*C07F 5/02* (2006.01)

(56) References Cited

U.S. PATENT DOCUMENTS

2007/0178554 A1    8/2007  Shiva et al.
2016/0311836 A1*  10/2016  Takenaka .............. C07C 251/24

FOREIGN PATENT DOCUMENTS

| | | | |
|---|---|---|---|
| CN | 105348309 | B | 5/2017 |
| CN | 108299479 | A | 7/2018 |
| CN | 109384806 | A | 2/2019 |
| EP | 2907818 | A1 | 8/2015 |
| EP | 3085687 | A1 | 10/2016 |
| EP | 3251698 | A1 | 12/2017 |
| JP | 2009051766 | A | 3/2009 |
| JP | 2016204314 | A | 12/2016 |
| RU | 2660433 | C2 | 7/2018 |
| WO | WO-2007096186 A1 * | | 8/2007 ........... C07D 211/22 |
| WO | 2014061508 | A1 | 4/2014 |
| WO | 2015093469 | A1 | 6/2015 |
| WO | WO-2021244529 A1 * | | 12/2021 |

OTHER PUBLICATIONS

Falco-Magnus et al. Organic Letters 2010 12 (17), 3870-3873 (Year: 2010).*

Adelphe M. Mfuh et al., Additive- and Metal-Free, Predictably 1,2- and 1,3-Regioselective, Photoinduced Dual C-H/C-X-Borylation of Haloarenes, J. Am. Chem. Soc., 2016.

Kiichi Ishiwata et al., Synthesis and Radiation Dosimetry of 4-Borono-2-r Flfluoro-D,L-phenylalanine: a Target Compound for PET and Boron Neutron Capture Therapy, Appl. Radiat. Isot. vol. 42, No. 4, pp. 325-328, 1991, Int. J. Radial. Appl. Instrum. Part A.

Andrew V. Mossine et al., Synthesis of [18F]Arenes via the Copper-Mediated [18F]Fluorination of Boronic Acids, Org. Lett., 2015, 17, 23, 5780-5783.

Kiichi Ishiwata et al., Synthesis and Radiation Dosimetry of 4-Borono-2-r Flfluoro-D, L-phenylalanine: a Target Compound for PET and Boron Neutron Capture Therapy, Appl. Radiat. Isot. vol. 42, No. 4, pp. 325-328, 1991.

Tert-butyl 2-amino-3-(2,4-difluorophenyl)propanoate, D6 PubChem CID 83225402, Oct. 20, 2014, found in the PubChem database on Dec. 21, 2021.

* cited by examiner

METHOD FOR PREPARING $^{18}$F-BPA AND INTERMEDIATE

RELATED APPLICATION INFORMATION

This application is a continuation application of U.S. patent application Ser. No. 17/171,224, filed on Feb. 9, 2021 and currently pending, which itself is a continuation application of International Application No. PCT/CN2019/100678, filed on Aug. 15, 2019, which claims priority to Chinese Patent Application No. 201810940708.3, filed on Aug. 17, 2018; Chinese Patent Application No. 201811478615.X, filed on Dec. 5, 2018; and Chinese Patent Application No. 201811478614.5, filed on Dec. 5, 2018, the disclosures of which are hereby incorporated by reference.

FIELD OF THE DISCLOSURE

The present disclosure relates to the field of pharmaceutical and chemical synthesis, and more particularly to a method for preparing $^{18}$F-BPA and an intermediate.

BACKGROUND OF THE DISCLOSURE

Malignant tumors are major diseases that seriously endanger human health and life. At present, the treatments of the malignant tumors are mainly through radiotherapy or chemotherapy. Boron neutron capture therapy (BNCT) uses nuclear reactions that occur in tumor cells to destroy cancer cells. By using the characteristics of high capture cross section of boron ($^{10}$B)-containing drugs for thermal neutrons, two heavy charged particles of $^{4}$He and $^{7}$Li are generated by $^{10}$B(n,α)$^{7}$Li neutron capture and nuclear fission reactions. The two charged particles have an average energy of about 2.33 MeV, and the characteristics of high linear energy transfer (LET) and short range. The LET and range of α particles are 150 keV/μm and 8 μm respectively, while the LET and range of $^{7}$Li heavy charged particles are 175 keV/μm and 5 μm respectively. The total range of the two particles is about the size of a cell, and therefore the radiation damage to organisms can be limited to a cellular level. When the boron-containing drugs are selectively aggregated in tumor cells, the tumor cells can be locally killed by selecting an appropriate neutron radiation source, without causing too much damage to normal tissues. Because the effect of BNCT depends on the concentration of the boron-containing drugs and the number of the thermal neutrons at tumor cell sites, BNCT is also referred to as a binary cancer therapy. It can be seen that, in addition to the development of the neutron source, the development of the boron-containing drugs plays an important role in the research of BNCT. 4-($^{10}$B)borono-L-phenylalanine (L-$^{10}$BPA) is a boron-containing drug for BNCT treatment of cancer, which exhibits good therapeutic effects in treating various malignant tumors, such as glioblastoma multiforme and melanoma. The treatment planning of BNCT is established based on the result of 2-fluoro-4-borono-L-phenylalanine ($^{18}$F-BPA) for tumor targeting, by using BPA labeled with a positron radionuclide of $^{18}$F in combination with a positron emission tomography (PET) to diagnose brain tumors and other types of solid tumors.

CN105916836A discloses a method for preparing 2-fluoro-4-borono-L-phenylalanine and a precursor of 2-fluoro-4-borono-L-phenylalanine. This patent application describes the preparation of $^{18}$F-BPA by substituting a $^{18}$F ion for the leaving group on benzene ring to obtain $^{18}$F-labeled halogen-substituted phenylalanine compound, followed by a coupling reaction. In CN105348309B, after the benzene ring is labeled with $^{18}$F, $^{18}$F-BPA is obtained by the reaction of an aldehyde group on the benzene ring with phenylazolinone. In CN102887913B, $^{18}$F-BPA is obtained by substituting a $^{18}$F ion for the nitro group on benzene ring to provide a $^{18}$F-labeled iodine-substituted phenylalanine compound, followed by a coupling reaction. In the foregoing methods, the substitution reactions of boric esters are all performed after $^{18}$F labeling, which have many reaction steps and a long preparation time.

Since the half-life of $^{18}$F is about 110 min, after $^{18}$F labeling, how to simplify the preparation steps and shorten the preparation time is a significant and challenging study, which is related to the radiochemical yield and application limitations of the synthesis. Therefore, it is extremely important for the application of $^{18}$F-BPA to develop a preparation method that is simple and efficient, has mild reaction conditions and high yield, and meets clinical needs.

The statements in this section merely provide background information related to the present disclosure and may not constitute prior art.

SUMMARY

An object of the present disclosure is to provide a method and intermediate for preparing 2-fluoro-4-borono-L-phenylalanine ($^{18}$F-BPA, F-BPA). The method for synthesizing $^{18}$F-BPA simplifies the synthesis steps after $^{18}$F labeling. The method is simple and efficient, has high yield and high product purity, and improves the radiochemical yield of the synthesis.

According to a first aspect, the present disclosure provides a method for preparing $^{18}$F-BPA having the structure:

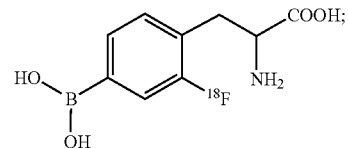 [SMILES: NC(Cc1ccc(B(O)O)cc1[18F])C(=O)O]

including using intermediate I, the intermediate I having the structure

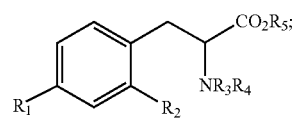

where $R_1$ or $R_2$ represents halogens, boric acid groups or substituents that is hydrolyzable to boric acid groups; $R_3$ or $R_4$ independently represents hydrogen, an amino-protecting group, or an imino group combined with an amino group for protecting the amino group; and $R_5$ represents hydrogen or a carboxyl-protecting group.

Implementations of this aspect may include one or more of the following features.

In another preferred embodiment, the intermediate I includes intermediate I-1 and intermediate I-2, where the intermediate I-1 has the structure:

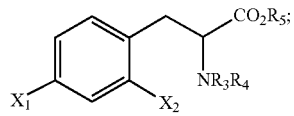
I-1 and the intermediate I-2 has the structure:

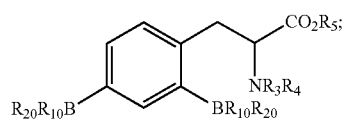
I-2 where both of $X_1$ and $X_2$ are halogens, and preferably, $X_1$ and $X_2$ represent Cl, Br, or I; $R_{10}$ and $R_{20}$ are OH, or taken together with the boron atom to which they are attached, represent a substituent that is hydrolyzable to a boric acid group; $R_3$ or $R_4$ independently represents hydrogen, an amino-protecting group, or an imino group combined with an amino group for protecting the amino group; and $R_5$ represents hydrogen or a carboxyl-protecting group.

In another preferred embodiment, $R_3$ or $R_4$ as an amino-protecting group includes an alkoxycarbonyl protecting group, an acyl protecting group, and an alkyl protecting group. Preferably, $R_3$ or $R_4$ as an amino-protecting group further includes substituents selected from the group consisting of benzyloxycarbonyl, tert-butyloxycarbonyl, fluorenylmethoxycarbonyl, allyloxycarbonyl, trimethylsilyl ethoxycarbonyl, methoxy (or ethoxy) carbonyl, phthaloyl, tosy, trifluoroacetyl, o- (or p-) nitrobenzenesulfonyl, pivaloyl, benzoyl, trityl, 2,4-dimethoxybenzyl, p-methoxybenzyl, and benzyl.

In another preferred embodiment, $R_3$ or $R_4$ as an amino-protecting group, taken together with N, forms a C=N bond, preferably, —$NR_3R_4$ is

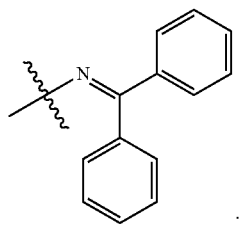 [SMILES: *N=C(c1ccccc1)c1ccccc1]

In another preferred embodiment, the substituent that is hydrolyzable to a boric acid group is a boric ester group. More preferably, —$BR_{10}R_{20}$ is a boric acid pinacol ester group, B is preferably $^{10}B$.

In another preferred embodiment, the carboxyl-protecting group includes a substituted or unsubstituted C1-20 alkyl group. The substituent includes phenyl, halogen, nitro, hydroxy, and methoxy. Preferably, the carboxyl-protecting group is a C1-10 alkyl, phenyl, and benzyl. Preferably, the carboxyl-protecting group includes a substituted or unsubstituted C1-C20 alkyl group; and the substituent includes phenyl, halogen, nitro, hydroxy, and methoxy, preferably, a C1-C10 alkyl, phenyl, and benzyl. Preferably, the carboxyl-protecting group further includes methyl, ethyl, isopropyl, tert-butyl, benzhydryl, benzyl, p-nitrobenzyl, p-methoxybenzyl, 4-pyridylbenzyl, trichloroethyl, methylthioethyl, p-toluenesulfonyl ethyl, p-nitrophenylthioethyl, phenyl, and benzyl.

In another preferred embodiment, the intermediate I is selected from the following compounds:

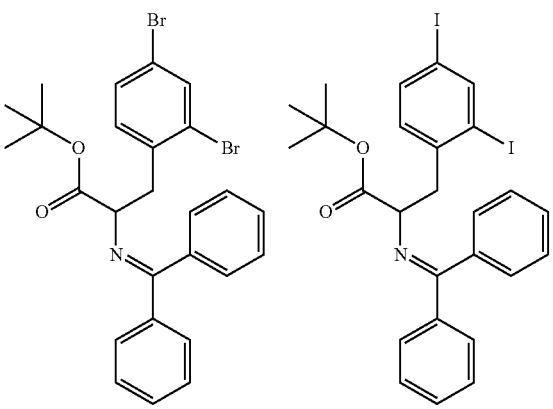

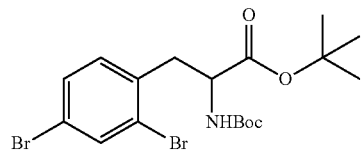

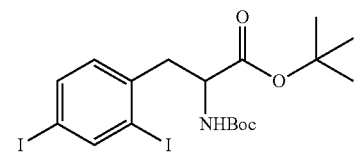

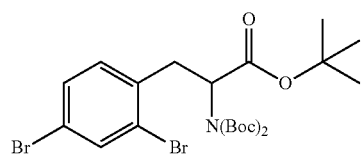

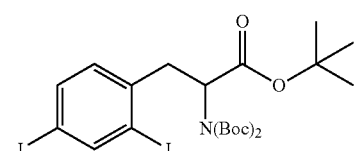

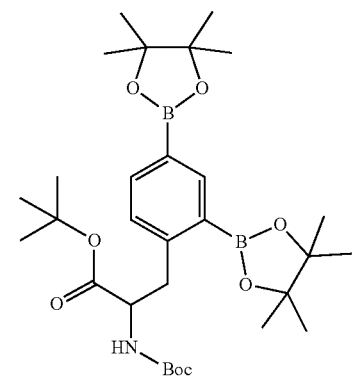

-continued

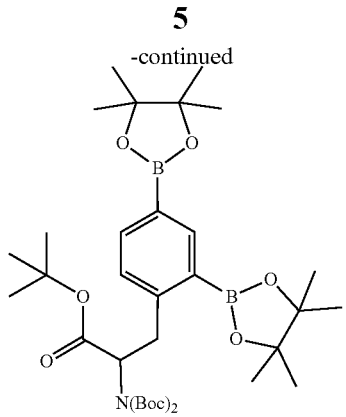

In another preferred embodiment, the method includes reacting the intermediate I-2 with a $^{18}$F ion to obtain a $^{18}$F-substituted compound

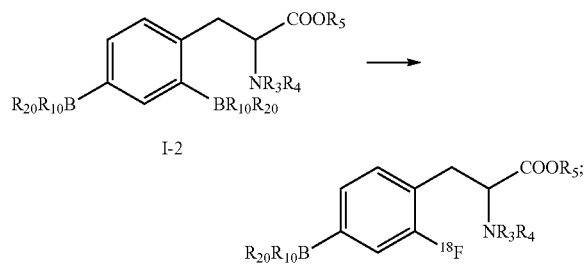

where $R_{10}$ and $R_{20}$ are OH, or taken together with the boron atom to which they are attached, represent a substituent that is hydrolyzable to a boric acid group; $R_3$ or $R_4$ independently represents hydrogen, an amino-protecting group, or an imino group combined with an amino group for protecting the amino group; and $R_5$ represents hydrogen or a carboxyl-protecting group.

In another preferred embodiment, the method includes deprotecting the $^{18}$F-substituted compound to obtain the $^{18}$F-BPA

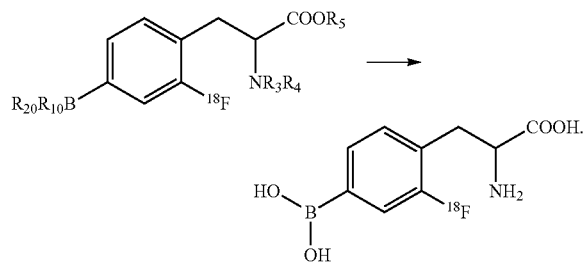

In another preferred embodiment, the reaction of the intermediate I-2 with the $^{18}$F ion further includes using a copper catalyst, with the copper catalyst preferably including Cu(OTf)$_2$Py$_4$ or Cu(OTf)$_2$.

In another preferred embodiment, the reaction of the intermediate I-2 with the $^{18}$F ion is carried out at a temperature of 20-150° C., preferably, at 100-130° C.

In another preferred embodiment, the reaction of the intermediate I-2 with the $^{18}$F ion is carried out in a solvent including water, methanol, DMF, DMA, DMSO, acetonitrile, n-butanol, ethanol, dichloromethane, or any mixed solvents thereof.

In another preferred embodiment, the intermediate I-1 is reacted with a boric acid or boric ester to obtain the intermediate I-2

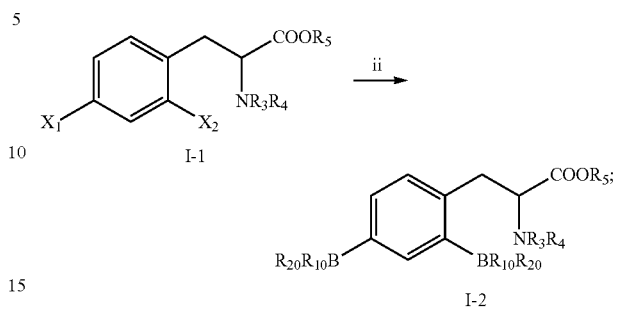

where both of $X_1$ and $X_2$ are halogens, and preferably, $X_1$ and $X_2$ represent Cl, Br, or I; $R_{10}$ and $R_{20}$ are OH, or taken together with the boron atom to which they are attached, represent a substituent that is hydrolyzable to a boric acid group; $R_3$ or $R_4$ independently represents hydrogen, an amino-protecting group, or an imino group combined with an amino group for protecting the amino group; and $R_5$ represents hydrogen or a carboxyl-protecting group.

In another preferred embodiment, the intermediate I-1 is reacted with a boric acid or boric ester under nitrogen protection.

In another preferred embodiment, the intermediate I-1 is reacted with a boric acid or boric ester at 20-100° C., preferably, at 50-100° C.

A palladium catalyst is not particularly limited. Preferably, the palladium catalyst is selected from the group consisting of tris(dibenzylideneacetone)dipalladium (Pd$_2$(dba)$_3$), tetrakis(triphenylphosphine)palladium (Pd(PPh$_3$)$_4$), palladium acetate, palladium chloride, dichlorobis(triphenylphosphine), palladium trifluoroacetate, palladium triphenylphosphine, [1,1'-bis(diphenylphosphino)ferrocene] palladium dichloride, bis(tri-o-tolylphosphine) palladium dichloride, [1,2-Bis(diphenylphosphino)ethane] palladium dichloride, or a combination thereof.

The boric ester is not particularly limited. Preferably, the boric ester is selected from the group consisting of bis(pinacolato)diboron, bis(catecholato)diboron, bis(3,3-dimethyl-2,4-pentanediol)boric ester, triethanolamine boric ester, trimethyl boric ester, triisopropyl boric ester, triethyl boric ester, tributyl boric ester, bis(neopentyl glycolato) diboron, or a combination thereof.

In another preferred embodiment, the method further includes chirally resolving the intermediate I-1 to obtain compound I-1a in L configuration and compound I-1b in D configuration, and then reacting the compound I-1a and the compound I-1b with a boric acid or boric ester respectively.

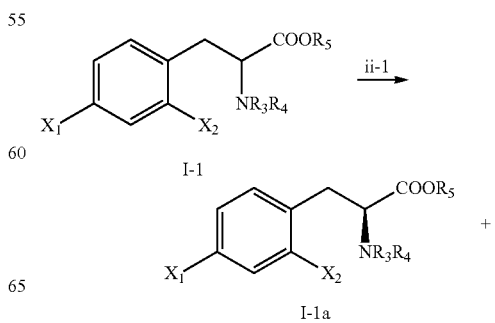

-continued

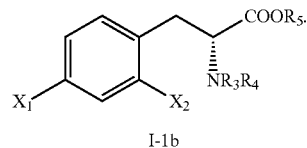

I-1b

In another preferred embodiment, the method further includes i) reacting intermediate II with intermediate III to obtain the intermediate I-1

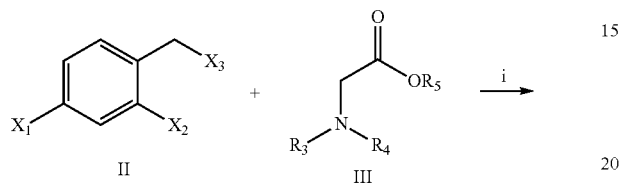

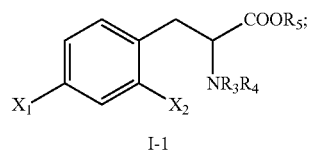

I-1 where $X_1$, $X_2$, and $X_3$ are each independently halogens, preferably, $X_1$, $X_2$, and $X_3$ represent Cl, Br, or I; $R_3$ or $R_4$ independently represents hydrogen or an amino-protecting group, or an imino group combined with an amino group for protecting the amino group; and $R_5$ represents hydrogen or a carboxyl-protecting group.

In another preferred embodiment, the intermediate III is

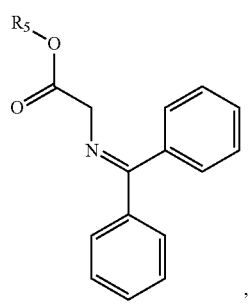

, and the intermediate I-1 is

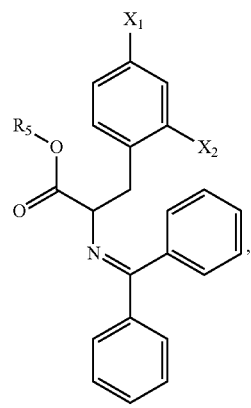

, where $X_1$ and $X_2$ are halogens, preferably, $X_1$ and $X_2$ represent Cl, Br, or I; and $R_5$ represents hydrogen or a carboxyl-protecting group.

In another preferred embodiment, the method further includes deprotecting the amino group in the intermediate I-1 by hydrolyzing under acidic conditions, reacting with $Boc_2O$ under basic conditions, protecting the amino group in the intermediate I-1 with Boc to obtain the compound

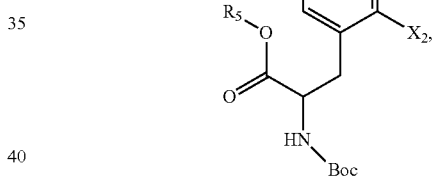

and then reacting with a boric acid or boric ester, where the reaction is preferably performed at room temperature, and $R_5$ represents preferably a C1-10 alkyl group.

According to a second aspect, the present disclosure provides an intermediate I, having the structure

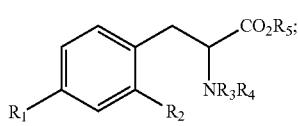

I where $R_1$ or $R_2$ represents halogens, boric acid groups or substituents that are hydrolyzable to boric acid groups;
$R_3$ or $R_4$ independently represents hydrogen, an amino-protecting group, or an imino group combined with an amino group for protecting the amino group; and
$R_5$ represents hydrogen or a carboxyl-protecting group.

Implementations of this aspect may include one or more of the following features.

In another preferred embodiment, the intermediate I includes intermediate I-1 and intermediate I-2, where the intermediate I-1 has the structure:

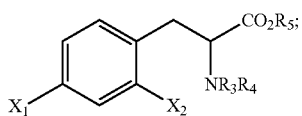

and the intermediate I-2 has the structure:

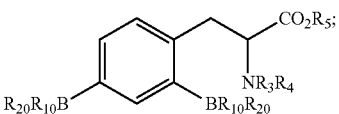

where both of $X_1$ and $X_2$ are halogens; B represents boron, preferably, $^{10}B$; $R_{10}$ and $R_{20}$ are OH, or taken together with the boron atom to which they are attached, represent a substituent that is hydrolyzable to a boric acid group; $R_3$ or $R_4$ independently represents hydrogen, an amino-protecting group, or an imino group combined with an amino group for protecting the amino group; and $R_5$ represents hydrogen or a carboxyl-protecting group.

In another preferred embodiment, the substituent that is hydrolyzable to a boric acid group is a boric ester group, preferably, a boric acid pinacol ester group; $R_3$ or $R_4$ includes an alkoxycarbonyl protecting group, an acyl protecting group, and an alkyl protecting group; and $R_5$ includes a substituted or unsubstituted C1-20 alkyl, preferably, tert-butyl.

In another preferred embodiment, the intermediate I is selected from the following compounds:

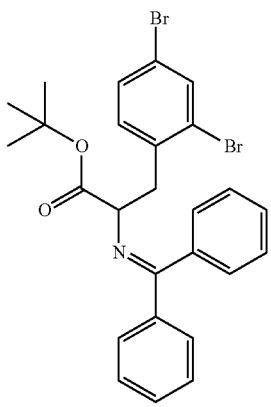

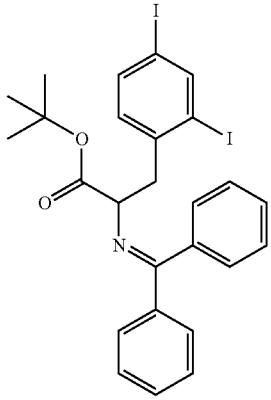

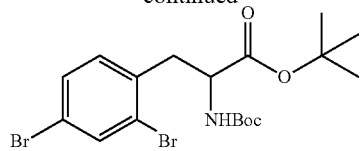

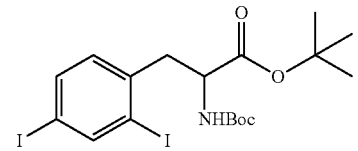

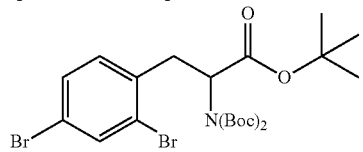

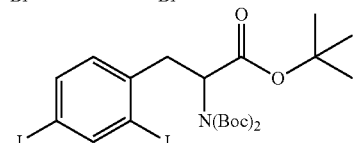

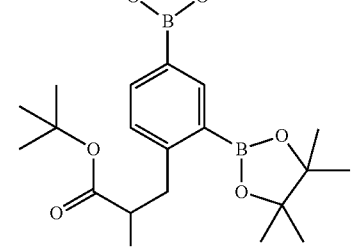

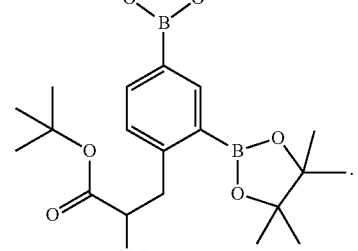

According to a third aspect, the present disclosure provides a use of the intermediate I according to the second aspect for preparing $^{18}F$-BPA, wherein the $^{18}F$-BPA has the structure:

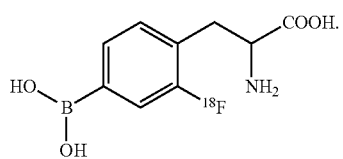 [SMILES: NC(Cc1ccc(B(O)O)cc1[18F])C(=O)O]

It should be understood that, within the scope of the present disclosure, the foregoing technical features of the present disclosure and the technical features specifically described in the following (such as the embodiments) can be combined with each other to form a new or preferred technical solution. For the sake of brevity, details are not described herein again.

Further areas of applicability will become apparent from the description provided herein. It should be understood that the description and specific examples are intended for purposes of illustration only and are not intended to limit the scope of the present disclosure.

Figure 1:
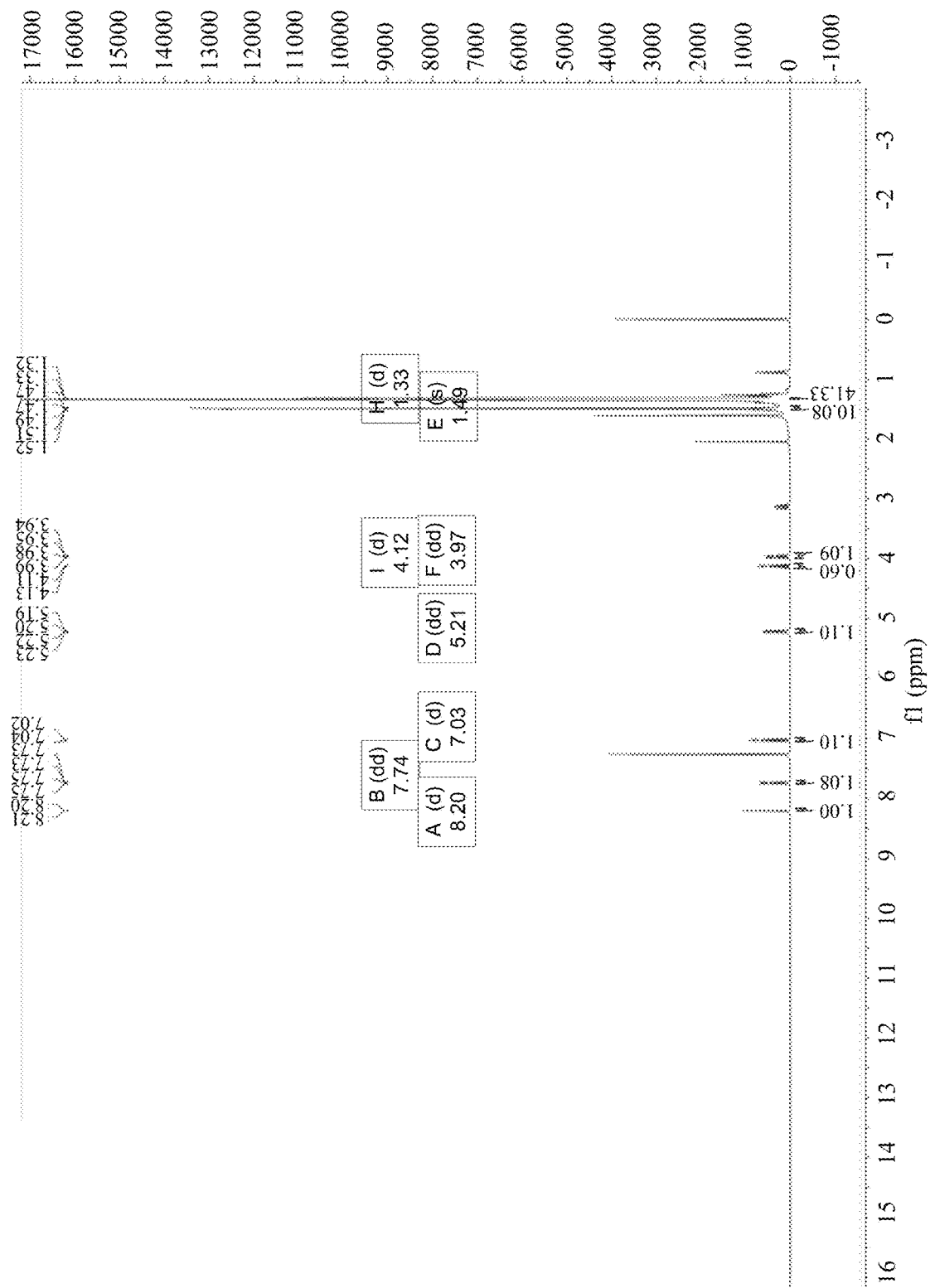
FIG. 1 is the $^1$H-NMR spectrum of N,N-bis(tert-butoxycarbonyl)-2,4-bis(4,4,5,5-tetramethyl-1,3,2-dioxaborolan-2-yl)-phenylalanine tert-butyl ester prepared in Example 6.

The drawings described herein are for illustrative purposes only of selected embodiments and not all possible implementations, and are not intended to limit the scope of the present disclosure. Corresponding reference numerals indicate corresponding parts throughout the several views of the drawings.

DETAILED DESCRIPTION

After extensive and in-depth research, the inventor prepared an intermediate for preparing $^{18}$F-BPA. The intermediate includes a bis(pinacolato)diboron-substituted phenylalanine intermediate. $^{18}$F-BPA may be obtained by substituting $^{18}$F for a boric acid pinacol ester group at the ortho position of the alanine group. The method shortens the steps of preparing $^{18}$F-BPA after $^{18}$F labeling, which is simple and efficient, has high yield and high product purity, and improves the radiochemical yield of the synthesis. The present disclosure is made on such basis.

Terminology

Unless otherwise defined, all scientific and technological terms herein have the same meanings as commonly understood by those skilled in the art to which the claims belong. Unless otherwise specified, all patents, patent applications, and publications cited in this specification are incorporated herein by reference in their entirety.

It should be understood that the above brief description and the following detailed description are exemplary and only used for explanation, and are not intended to limit the subject of the present disclosure. In this disclosure, unless otherwise specified, the plural forms are included when the singular form is used. It should be noted that, unless otherwise clearly specified in this specification, the singular form used in this specification and claims includes the plural referents. It is also noted that, unless otherwise specified, the use of "or", "alternatively" means "and/or". In addition, the terms "comprise", "include", and other grammatical forms such as "comprising", "including" and "having" are not limiting.

When a substituent is described by a conventional chemical formula written from left to right, the substituent also includes chemically equivalent substituents obtained when the structural formula is written from right to left. For example, —CH$_2$O— is equivalent to —OCH$_2$—.

The section titles used herein are only for the purpose of organizing the article, and should not be construed as a limitation on the subject. All documents or parts of the documents cited in this disclosure, including but not limited to patents, patent applications, articles, books, operating manuals, and papers, are incorporated herein by reference in their entirety.

In addition to the foregoing, when used in the specification and claims of this disclosure, unless otherwise specified, the following terms have the following meanings.

In this disclosure, the term "halogen" refers to F, Cl, Br, and I. "F" refers to fluorine, including radioactive and non-radioactive fluorine, such as $^{18}$F and $^{19}$F, preferably, $^{18}$F. "B" refers to boron, including radioactive and non-radioactive boron, preferably, $^{10}$B. "N" refers to nitrogen. "Nitro" refers to —NO$_2$ group. "Amino" refers to —NH$_2$ group. "Boric acid group" refers to —B(OH)$_2$ group.

In this disclosure, the term "alkyl", as a group or a part of other groups (for example, in a halogen-substituted alkyl group, etc.), refers to a straight or branched hydrocarbon chain group consisting only of carbon and hydrogen atoms, without unsaturated bonds, having, for example, 1 to 10 carbon atoms, and connected to the rest of the molecule by a single bond. Examples of the alkyl group include, but are not limited to methyl, ethyl, n-propyl, isopropyl, n-butyl, and the like. The term "C1-10 alkyl group" refers to the alkyl group having 1-10 carbon atoms, such as methyl, ethyl, propyl, isopropyl, pentyl, and the like.

Preferably, the inert solvent is selected from the group consisting of toluene, benzene, water, methanol, ethanol, isopropanol, ethylene glycol, N-methylpyrrolidone, dimethyl sulfoxide, tetrahydrofuran, dichloromethane, chloroform, 1,2-dichloroethane, acetonitrile, N,N-dimethylformamide, N,N-dimethylacetamide, dioxane, or a combination thereof. More preferably, the inert solvent is a mixed solvent of benzene and water.

The term "substituent that is hydrolyzable to a boric acid group" represents a substituent that may generate a boric acid group (—B(OH)$_2$) after hydrolysis, for example, a boric ester group. The substituent includes, but is not limited to the following substituents:

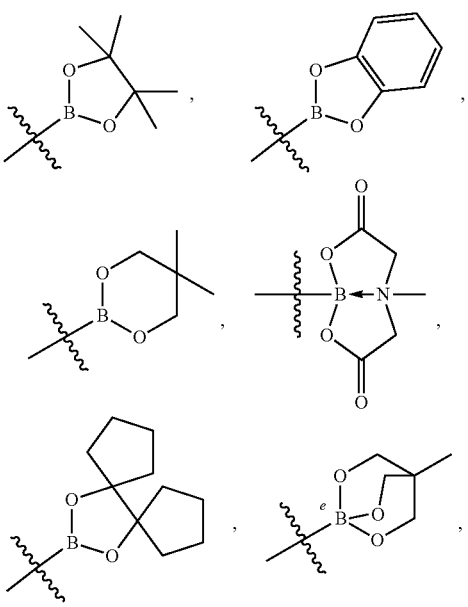

-continued

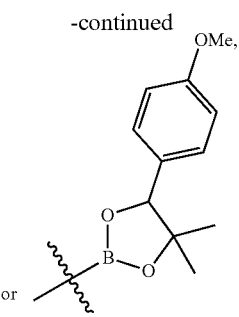

or and preferably, a boric acid pinacol ester group.

In the present disclosure, $R_3$ or $R_4$ as an amino-protecting group may be independently protecting groups, including but not limited to, an alkoxycarbonyl protecting group, an acyl protecting group, and an alkyl protecting group, or $R_3$ or $R_4$ may also combine with N to form imino (C═N) for protecting the amino group, for example,

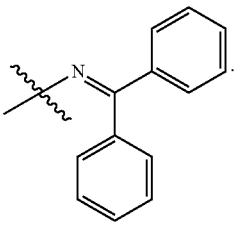 [SMILES: *N=C(c1ccccc1)c1ccccc1]

The above two forms of protecting groups should fall within the scope of the "amino-protecting group" in the present disclosure. Among those protecting groups, the alkoxycarbonyl protecting group includes, but is not limited to: benzyloxycarbonyl (Cbz), tert-butyloxycarbonyl (Boc), fluorenylmethoxycarbonyl (Fmoc), allyloxycarbonyl (Alloc), trimethylsilyl ethoxycarbonyl (Teoc), and methoxycarbonyl or ethoxycarbonyl. The acyl protecting group includes, but is not limited to: phthaloyl (Pht), tosyl (Tos), trifluoroacetyl (Tfa), o-(p-) nitrobenzenesulfonyl (Ns), pivaloyl, and benzoyl. The alkyl protecting group includes, but is not limited to: trityl (Trt), 2,4-dimethoxybenzyl (Dmb), p-methoxybenzyl (PMB), and benzyl (Bn).

The term "carboxyl-protecting group" refers to a protecting group that may combine with carboxyl to form ester group, amide, or hydrazide, including but not limited to alkyl, phenyl, and alkyl-substituted amino. "Alkyl" is preferably a straight or branched and substituted or unsubstituted alkyl with a substituent having 1-20 carbon atoms, such as methyl, ethyl, isopropyl, tert-butyl, benzhydryl, benzyl, p-nitrobenzylp, p-methoxybenzyl, 4-pyridylbenzyl, trichloroethyl, methylthioethyl, p-toluenesulfonylethyl, p-nitrophenylthioethyl, and the like.

In this disclosure, "optional" or "optionally" represents that the event or condition described later may or may not occur, and the description includes both the occurrence and non-occurrence of the event or condition. For example, "optionally substituted aryl group" represents that the aryl group is substituted or unsubstituted, and the description includes both the substituted aryl group and the unsubstituted aryl group.

The present disclosure will include various stereoisomers and mixtures thereof. The "stereoisomers" refer to compounds consisting of the same atoms bonded by the same bonds, but having different three-dimensional structures. All tautomeric forms of the compounds of the present disclosure will also be included in the scope of the present disclosure. "Tautomer" refers to an isomer formed by transferring a proton from one atom of a molecule to another atom of the same molecule.

The intermediate compounds of the present disclosure contain chiral carbon atoms, and therefore may generate enantiomers, diastereomers, and other stereoisomeric forms. Each chiral carbon atom may be defined as (R)- or (S)-based on stereochemistry. The present disclosure is intended to include all possible isomers, as well as their racemates and optically pure forms. For the preparation of the compounds of the present disclosure, racemates, diastereomers, or enantiomers may be selected as raw materials or intermediates. Optically active isomers may be prepared by using chiral synthons or chiral reagents, or resolved by using conventional techniques, such as crystallization and chiral chromatography. The "intermediate" of the present disclosure has both L-configuration phenylalanine structure and D-configuration phenylalanine structure, which are encompassed within the protection scope of the present disclosure.

Preparation method for $^{18}$F-BPA

The present disclosure describes a new method for preparing $^{18}$F-BPA, for example, by using the methods shown in following examples, but is not limited to the exemplary methods. The amino- and carboxyl-protecting groups, and the boric ester group used in the following reaction scheme may be appropriately changed, and are not limited to the exemplary method.

The method includes reacting the intermediate I-2 with a $^{18}$F ion to obtain a $^{18}$F-substituted compound

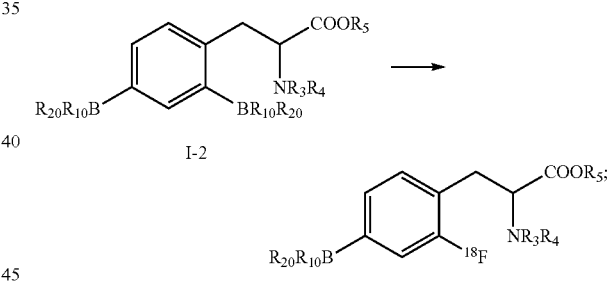

deprotecting the $^{18}$F-substituted compound, for example, by hydrolyzing the amino- and carboxyl-protecting group, and the boric ester group to obtain the $^{18}$F-BPA

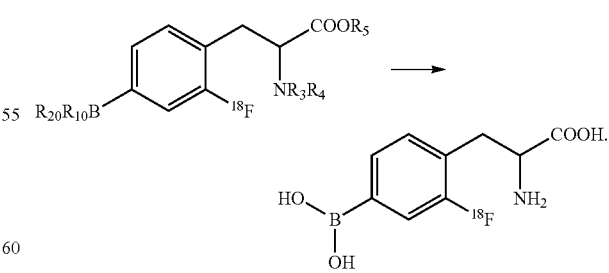

For each step, the reaction temperature may be appropriately selected depending on solvents, starting materials, and reagents, and the reaction time may also be appropriately selected depending on reaction temperatures, solvents, starting materials, and reagents. After the reaction of each step is completed, a target compound may be separated and purified from a reaction system by conventional methods, such as filtration, extraction, recrystallization, washing, silica gel column chromatography, and the like. Without affecting the next reactions, the target compound may also directly used in the next steps without separation and purification.

In the step of synthesizing $^{18}$F-BPA with intermediate I, the $^{18}$F ion ([$^{18}$F]F$^-$) used may be obtained by bombarding H$_2$$^{18}$O with a proton beam through $^{18}$O(p, n) reaction, or by using methods known in the art. The $^{18}$F ion is captured on an ion exchange column, eluted with a K2.2.2/K$_2$CO$_3$ mixed solution, dried to remove water and then used for a labeling reaction. Intermediate I-2 is reacted with the $^{18}$F ion, and the resulting mixed solution is purified by a cation column, dried, and hydrolyzed to remove the amino- and carboxyl-protecting group, thereby obtaining the $^{18}$F-BPA. The reagent used includes hydrogen fluoride and potassium fluoride. The solvent used includes water, methanol, DMF, DMA, DMSO, acetonitrile, n-butanol, ethanol, dichloromethane, or any mixed solvents thereof. The reaction temperature is preferably 20-150° C., and more preferably, 100-130° C. The reaction time is preferably 5-60 minutes, and more preferably, 10-30 minutes. The drying may azeotropically remove water by adding a dry organic solvent. The organic solvent that may be used includes, but is not limited to: acetonitrile, dimethyl sulfoxide (DMSO), dimethylformamide (DMF), dimethylacetamide (DMA), or any combinations thereof. In a preferred implementation, a copper catalyst may be added to the reaction of the intermediate I and the $^{18}$F ion. The copper catalyst that may be used includes, but is not limited to: Cu(OTf)$_2$Py$_4$, Cu(OTf)$_2$, or a combination thereof.

It should be noted that the intermediate I and $^{18}$F-BPA in the present disclosure include all optical isomers thereof, including an isomer with an L-configuration phenylalanine structure and an isomer with a D-configuration phenylalanine structure. For example, $^{18}$F-BPA includes $^{18}$F-L-BPA having the L-configuration phenylalanine structure or $^{18}$F-D-BPA having the D-configuration phenylalanine structure. In the preparation method of the present disclosure, intermediate I may undergo chiral resolution to obtain a single-configuration compound for use in the reaction, or directly used in the reaction without resolution, to obtain $^{18}$F-BPA.

The present disclosure is further illustrated below with reference to specific examples. It should be understood that the following description is only the most preferred implementation of the present disclosure, and should not be considered as a limitation on the protection scope of the present disclosure. On the basis of a full understanding of the present disclosure, the experimental methods without specific conditions in the following examples are usually in accordance with the conventional conditions or in accordance with the conditions recommended by the manufacturer. A person skilled in the art may make non-essential changes to the technical solutions of the present disclosure, and such changes should be included in the protection scope of the present disclosure. Unless otherwise specified, the percentage and the parts are the percentage by weight and the parts by weight respectively.

Example 1 Preparation of N-Diphenylmethylene-2,4-Dibromophenylalanine Tert-Butyl Ester N-diphenylmethylene-glycine tert-butyl ester (40 g, 135.42 mmol, 1 eq), 1,4-dibromobenzyl bromide (44.53 g, 135.42 mmol, 1 eq), and tetra-n-butylammonium bromide (TBAB, 436.55 mg, 1.35 mmol, 0.01 eq) were dissolved in 300 mL of toluene, and 80 mL of a solution of potassium hydroxide (100.00 g, 1.78 mol, 13.16 eq) in water was added. The mixture was stirred at 25° C. for 12 hours until the reaction was complete. The reaction mixture was diluted with 100 mL of ethyl acetate, and then extracted with 400 mL (200 mL×2) of ethyl acetate. The organic phases were mixed, washed with 600 mL (300 mL×2) of saturated brine, dried with Na$_2$SO$_4$, and filtered to obtain a solid. The crude product was separated by column chromatography (petroleum ether/ethyl acetate=100: 1-20: 1) to obtain 15 g of product.

LCMS: MS (M+H$^+$)=544.0

$^1$H NMR: 400 MHz, CDCl$_3$

δ 7.56-7.46 (m, 3H), 7.35-7.16 (m, 7H), 7.01 (d, J=8.2 Hz, 1H), 6.59 (br d, J=6.8 Hz, 2H), 4.23 (dd, J=4.2, 9.5 Hz, 1H), 3.31 (dd, J=4.0, 13.4 Hz, 1H), 3.11 (dd, J=9.6, 13.5 Hz, 1H), 1.41-1.28 (m, 9H).

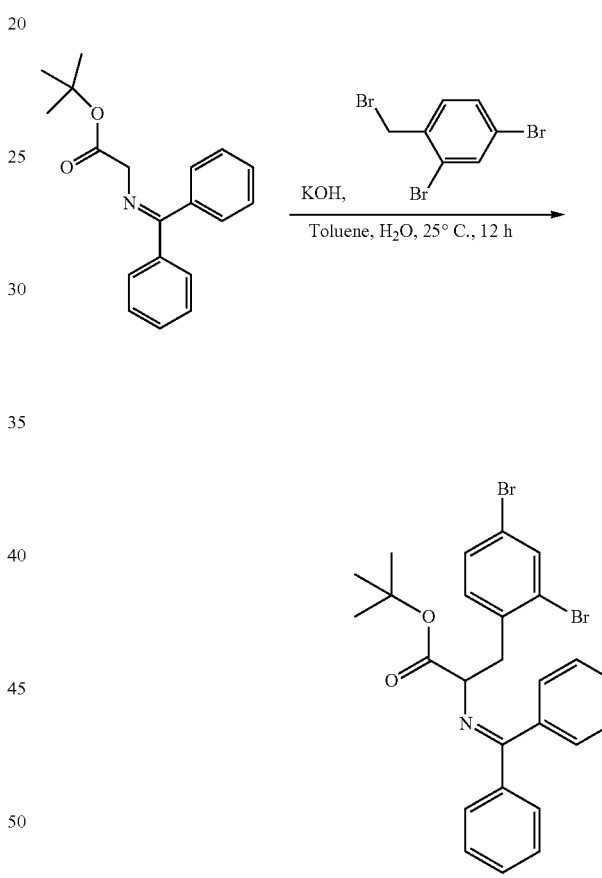

Example 2 Preparation of N-Tert-Butyloxycarbonyl-2,4-Dibromophenylalanine Tert-Butyl Ester N-diphenylmethylene-2,4-dibromophenylalanine tert-butyl ester (30 g, 55.22 mmol, 1 eq) was dissolved in THF (70 mL), and 20 mL aqueous citric acid (31.83 g, 165.66 mmol, 31.86 mL, 3 eq) was added, and stirred at 25° C. for 12 h. 50 mL of a solution of Na$_2$CO$_3$ (29.26 g, 276.10 mmol, 5 eq) in water and Boc$_2$O (13.26 g, 60.74 mmol, 13.95 mL, 1.1 eq) were added and stirred for additional 4 h. After the reaction was complete, the reaction mixture was extracted with 400 mL (200 mL×2) of ethyl acetate. The organic phases were mixed, washed with 400 mL (200 mL×2) of saturated brine, dried with Na₂SO₄, and filtered to obtain a solid. The crude product was separated by column chromatography (petroleum ether/ethyl acetate=100: 1-10: 1) to obtain 19.6 g of product (73.48% yield, 99.2% purity).

LCMS: MS (M-155⁺)=323.9

¹H NMR: 400 MHz, CDCl₃

δ7.72 (d, J=1.5 Hz, 1H, 7.37 (dd, J=1.8, 8.1 Hz, 1H), 7.13 (br d, J=8.1 Hz, 1H), 5.06 (br d, J=8.3 Hz, 1H), 4.59-4.38 (m, 1H), 3.23 (dd, J=5.9, 13.9 Hz, 1H), 3.00 (br dd, J=8.6, 13.8 Hz, 1H), 1.40 (br d, J=16.6 Hz, 17H).

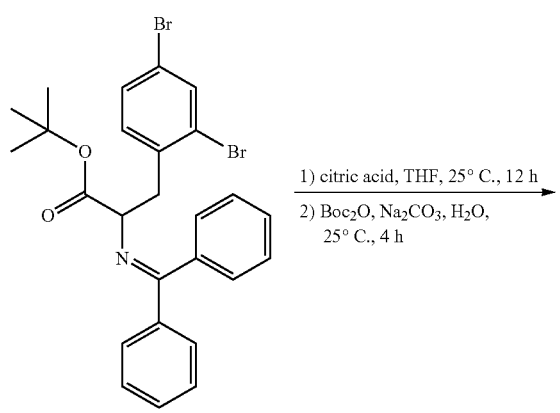

Example 3 Chiral Resolution of N-Tert-Butyloxycarbonyl-2,4-Dibromophenylalanine Tert-Butyl Ester 19.6 g of N-tert-butyloxycarbonyl-2,4-dibromophenylalanine tert-butyl ester was separated by SFC (column: DAICEL CHTRALPAK AY(250 mm*50 mm, 10 m); mobile phase: [0.1% NH₃H₂O MEOH]) to obtain 9.1 g of product (46.84% yield, 97.8% purity) and 9.2 g of product (48.18% yield, 99.5% purity).

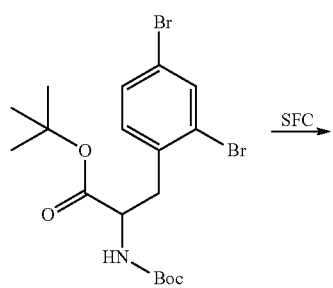

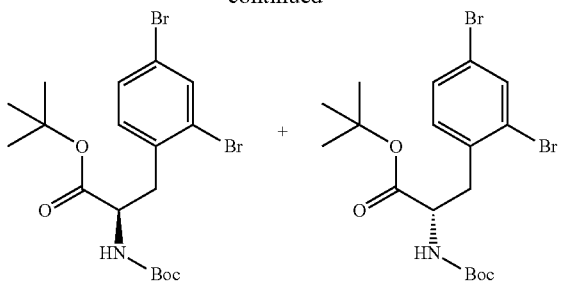

Example 4 Preparation of N-Tert-Butoxycarbonyl-2,4-Bis(4,4,5,5-Tetramethyl-1,3,2-dioxaborolan-2-yl)-phenylalanine tert-butyl ester N-tert-butyloxycarbonyl-2,4-dibromophenylalanine tert-butyl ester (7.50 g, 15.6 mmol, 1.00 eq), bis(pinacolato)diboron (19.8 g, 78.2 mmol, 5.00 eq), KOAc (6.14 g, 62.6 mmol, 4.00 eq), Pd(dppf)Cl₂ (1.15 g, 1.57 mmol, 0.10 eq), and dioxane (75.0 mL) were stirred under nitrogen protection at 90° C. for 1 h. After the reaction was complete, the resulting reaction mixture was filtered, and 200 mL of water was added. The reaction mixture was extracted with 300 mL (100 mL×3) of ethyl acetate. The organic phases were mixed, washed with 200 mL (100 mL×2) of saturated brine, dried with Na₂SO₄, and filtered to obtain a solid. The crude product was purified by HPLC to obtain 6.5 g of product (96.3% purity).

LCMS: MS (M+H⁺−156)=418.0

¹H NMR:400 MHz, CDCl₃

8.24 (s, 1H), 7.84 (d, J=7.6, 1H), 7.30 (d, J=7.6, 1H), 5.90 (d, J=8.4, 1H), 4.24-4.19 (m, 1H), 3.24-3.19 (m, 2H), 1.47 (s, 9H), 1.39 (s, 12H), 1.34 (s, 12H), 1.32 (s, 9H).

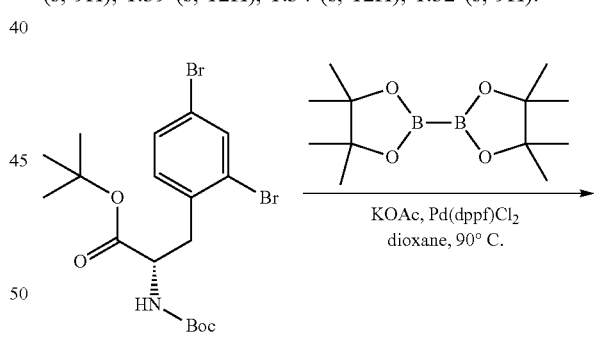

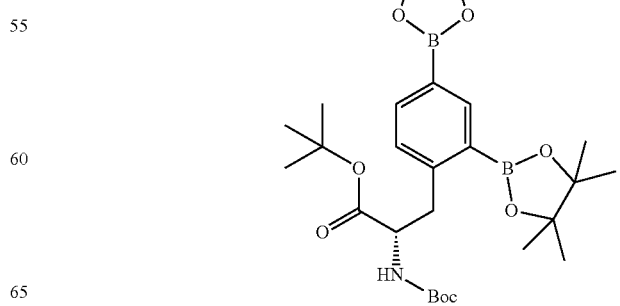

Example 5 Preparation of N-Tert-Butoxycarbonyl-2,4-Bis(4,4,5,5-Tetramethyl-1,3,2-dioxaborolan-2-yl)-phenylalanine tert-butyl ester O-tert-butyloxycarbonyl-2,4-dibromophenylalanine tert-butyl ester (7.00 g, 14.6 mmol, 1.00 eq), bis(pinacolato)diboron (18.5 g, 73.0 mmol, 5.00 eq), KOAc (5.73 g, 58.4 mmol, 4.00 eq), Pd(dppf)Cl$_2$ (5.73 g, 58.4 mmol, 4.00 eq), and dioxane (70.0 mL) were stirred under nitrogen protection at 90° C. for 3 h. After the reaction was complete, the resulting reaction mixture was filtered, and 200 mL of water was added. The reaction mixture was extracted with 300 mL (100 mL×3) of ethyl acetate. The organic phases were mixed, washed with 200 mL (100 mL×2) of saturated brine, dried with Na$_2$SO$_4$, and filtered to obtain a solid. The crude product was purified by HPLC to obtain 5.37 g of product (97.35% purity).

LCMS: MS (M-100-55+H$^+$): 418.3

$^1$HNMR: 400 MHz, CDCl$_3$

δ 1.31-1.35 (m, 21H), 1.39 (s, 12H), 1.47 (s, 9H), 3.16-3.29 (m, 2H), 4.19-4.26 (m, 1H), 5.89 (br d, J=8.40 Hz, 1H), 7.30 (d, J=8.00 Hz, 1H), 7.84 (dd, J=7.60, 1.47 Hz, 1H), 8.24 (s, 1H)

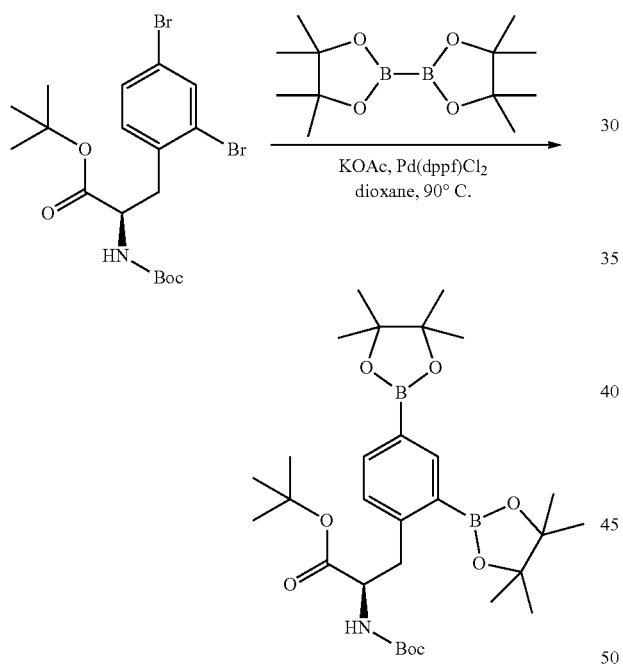

Example 6 Preparation of N,N-Bis(Tert-Butoxycarbonyl)-2,4-Bis(4,4,5,5-Tetramethyl-1,3,2-Dioxaborolan-2-Yl)-Phenylalanine Tert-Butyl Ester N-tert-butyloxycarbonyl-2,4-dibromophenylalanine tert-butyl ester (7.00 g, 14.6 mmol, 1.00 eq), bis(pinacolato)diboron (18.5 g, 73.0 mmol, 5.00 eq), KOAc (5.73 g, 58.4 mmol, 4.00 eq), Pd(dppf)Cl$_2$ (5.73 g, 58.4 mmol, 4.00 eq), and dioxane (70.0 mL) were stirred under nitrogen protection at 90° C. for 3 h. After the reaction was complete, the resulting reaction mixture was filtered, and 200 mL of water was added. The reaction mixture was extracted with 300 mL (100 mL×3) of ethyl acetate. The organic phases were mixed, washed with 200 mL (100 mL×2) of saturated brine, dried with Na$_2$SO$_4$, and filtered to obtain a solid. The crude product was purified by HPLC to obtain 5.37 g of product (97.35% purity). $^1$H NMR spectrum was shown in FIG. 1.

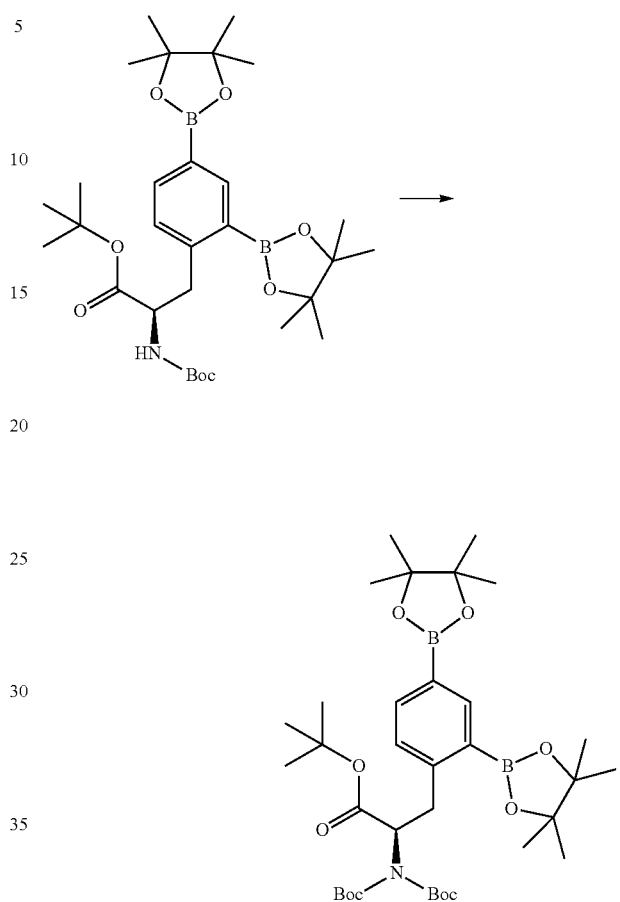

Example 7 Preparation of $^{18}$F-BPA

H$_2$$^{18}$O was irradiated with accelerated protons to obtain $^{18}$F ions through $^{18}$O(p, n) reaction. The ions were captured on an ion exchange column, eluted with a K2.2.2/K$_2$CO$_3$ mixed solution, dried to remove water and then used for a labeling reaction. The compound obtained in Example 5 was reacted with the $^{18}$F ions in DMA solution in the presence of Cu(OTf)$_2$Py$_4$ for 15 min. After the reaction was complete, the mixed solution was purified by a cation column and dried. The reaction was performed in HCl solution at 110° C. for 10 min, and NaOH solution was added for neutralization. The amino- and carboxyl-protecting groups were removed by hydrolyzation to obtain the crude product. The crude product was purified by HPLC to obtain $^{18}$F-BPA with a purity higher than 99%.

Figure 2:
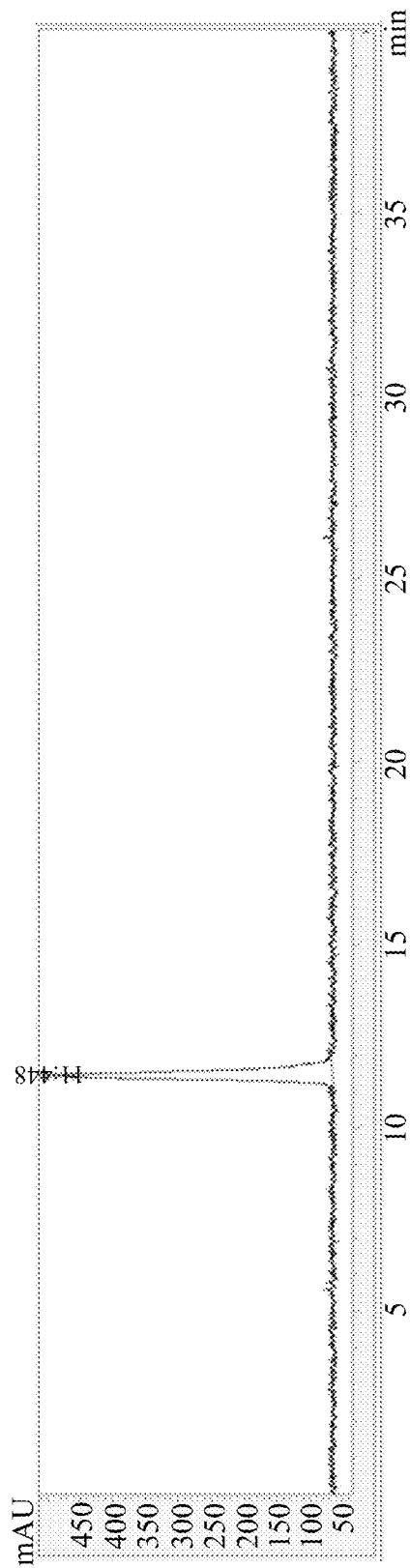
FIG. 2 is the Radio-HPLC chromatogram of $^{18}$F-BPA according to the present disclosure.
Figure 3:
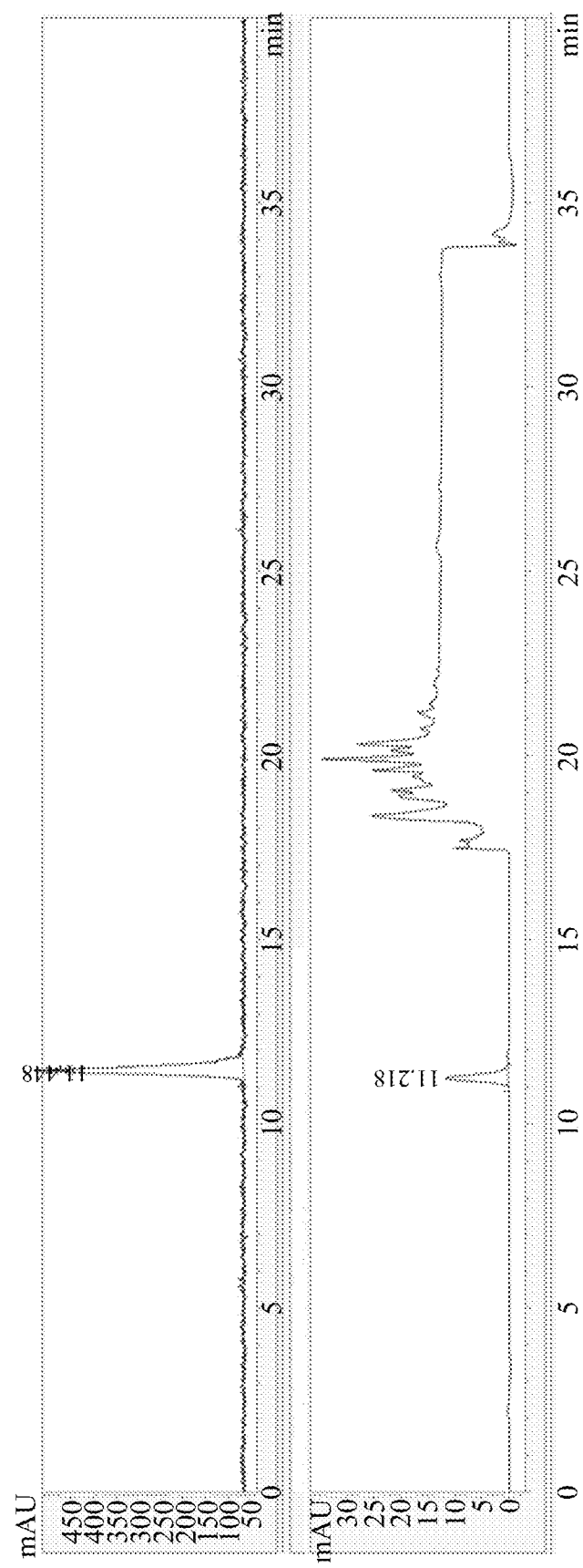
FIG. 3 is the Radio-HPLC chromatogram of $^{18}$F-BPA according to the present disclosure mixed with the standard $^{19}$F-BPA.

Radio-HPLC chromatogram was shown in FIG. 2. The product was mixed with a small amount of standard $^{19}$F-BPA and co-injected into the HPLC column. Under the same conditions, a peak appeared at the retention time (retention time 11 min±1 min), suggesting that the labeled product was $^{18}$F-BPA. See FIG. 3.

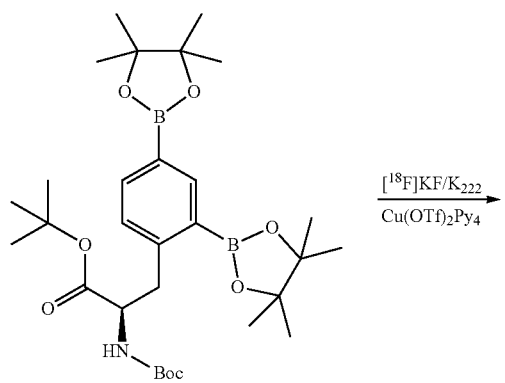

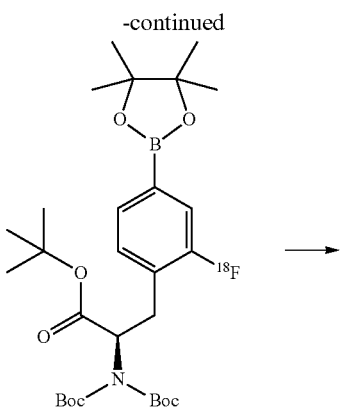

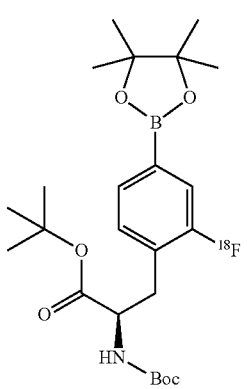

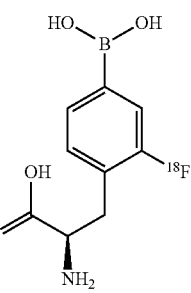

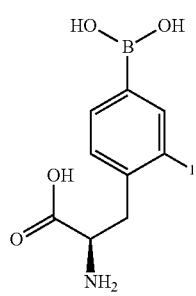

By using the same preparation method above, $^{18}$F-BPA was prepared from the compound obtained in Example 6, and $^{18}$F-BPA with a purity higher than 99% may also be obtained.

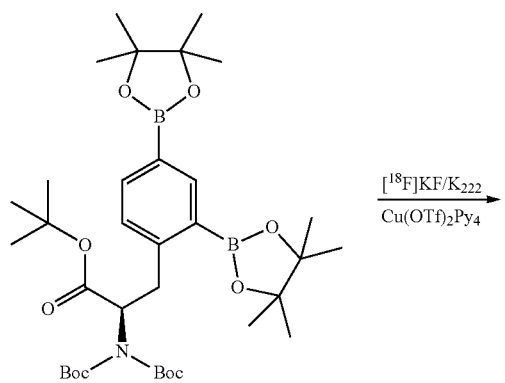

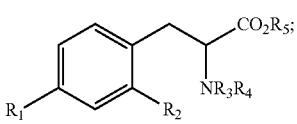

All documents mentioned in the present disclosure are incorporated by reference, as if each document is individually incorporated by reference. In addition, it should be understood that, after reading the above teaching of the present disclosure, those skilled in the art can make various changes or modifications to the present disclosure, and these equivalent forms also fall within the scope defined by the appended claims of this disclosure.

What is claimed is:

1. An intermediate I of the structure where $R_1$ represents boric acid groups or substituents that is hydrolyzable to boric acid groups;

$R_2$ represents boric acid groups or substituents that is hydrolyzable to boric acid groups;

$R_3$ represents hydrogen, an amino-protecting group, or an imino group combined with an amino group for protecting the amino group;

$R_4$ represents hydrogen, an amino-protecting group, or an imino group combined with an amino group for protecting the amino group; and $R_5$ represents hydrogen or a carboxyl-protecting group.

2. The intermediate I according to claim 1, wherein the intermediate I is intermediate I-2, and the intermediate I-2 is the structure:

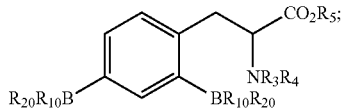

where

B represents boron;

$R_{10}$ and $R_{20}$ are OH, or taken together with the boron atom to which they are attached, represent a substituent that is hydrolyzable to a boric acid group;

$R_3$ represents hydrogen, an amino-protecting group, or an imino group combined with an amino group for protecting the amino group;

$R_4$ represents hydrogen, an amino-protecting group, or an imino group combined with an amino group for protecting the amino group; and $R_5$ represents hydrogen or a carboxyl-protecting group.

3. The intermediate I according to claim 1, wherein each boron is $^{10}B$.

4. The intermediate I according to claim 2, wherein each B is $^{10}B$.

5. The intermediate I according to claim 1, wherein each substituent that is hydrolyzable to a boric acid group is a boric ester group; $R_3$ is selected from the group consisting of an alkoxycarbonyl protecting group, an acyl protecting group, and an alkyl protecting group; $R_4$ is selected from the group consisting of an alkoxycarbonyl protecting group, an acyl protecting group, and an alkyl protecting group; and $R_5$ is a substituted or unsubstituted C1-20 alkyl group.

6. The intermediate I according to claim 2, wherein each substituent that is hydrolyzable to a boric acid group is a boric ester group; $R_3$ is selected from the group consisting of an alkoxycarbonyl protecting group, an acyl protecting group, and an alkyl protecting group; $R_4$ comprise is selected from the group consisting of an alkoxycarbonyl protecting group, an acyl protecting group, and an alkyl protecting group; and $R_5$ is a substituted or unsubstituted C1-20 alkyl group.

7. The intermediate I according to claim 2, wherein each —$BR_{10}R_{20}$ is a boric acid pinacol ester group.

8. The intermediate I according to claim 1, wherein $R_3$ is selected from the group consisting of benzyloxycarbonyl, tert-butyloxycarbonyl, fluorenylmethoxycarbonyl, allyloxycarbonyl, trimethylsilyl ethoxycarbonyl, methoxy carbonyl, ethoxy carbonyl, phthaloyl, tosy, trifluoroacetyl, o-nitrobenzenesulfonyl, p-nitrobenzenesulfonyl, pivaloyl, benzoyl, trityl, 2,4-dimethoxybenzyl, p-methoxybenzyl, and benzyl; and $R_4$ is selected from the group consisting of benzyloxycarbonyl, tert-butyloxycarbonyl, fluorenylmethoxycarbonyl, allyloxycarbonyl, trimethylsilyl ethoxycarbonyl, methoxy carbonyl, ethoxy carbonyl, phthaloyl, tosy, trifluoroacetyl, o-nitrobenzenesulfonyl, p-nitrobenzenesulfonyl, pivaloyl, benzoyl, trityl, 2,4-dimethoxybenzyl, p-methoxybenzyl, and benzyl.

9. The intermediate I according to claim 2, wherein $R_3$ is selected from the group consisting of benzyloxycarbonyl, tert-butyloxycarbonyl, fluorenylmethoxycarbonyl, allyloxycarbonyl, trimethylsilyl ethoxycarbonyl, methoxy carbonyl, ethoxy carbonyl, phthaloyl, tosy, trifluoroacetyl, o-nitrobenzenesulfonyl, p-nitrobenzenesulfonyl, pivaloyl, benzoyl, trityl, 2,4-dimethoxybenzyl, p-methoxybenzyl, and benzyl; and $R_4$ is selected from the group consisting of benzyloxycarbonyl, tert-butyloxycarbonyl, fluorenylmethoxycarbonyl, allyloxycarbonyl, trimethylsilyl ethoxycarbonyl, methoxy carbonyl, ethoxy carbonyl, phthaloyl, tosy, trifluoroacetyl, o-nitrobenzenesulfonyl, p-nitrobenzenesulfonyl, pivaloyl, benzoyl, trityl, 2,4-dimethoxybenzyl, p-methoxybenzyl, and benzyl.

10. The intermediate I according to claim 1, wherein —$NR_3R_4$ is

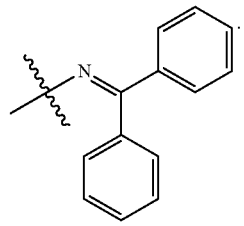 [SMILES: *N=C(c1ccccc1)c1ccccc1]

11. The intermediate I according to claim 2, wherein —$NR_3R_4$ is

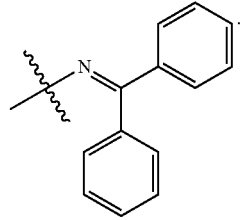 [SMILES: *N=C(c1ccccc1)c1ccccc1]

12. The intermediate I according to claim 1, wherein $R_5$ is a substituted or unsubstituted C1-20 alkyl group.

13. The intermediate I according to claim 2, wherein $R_5$ is a substituted or unsubstituted C1-20 alkyl group.

14. The intermediate I according to claim 1, wherein $R_5$ is C1-10 alkyl, phenyl, or benzyl.

15. The intermediate I according to claim 2, wherein $R_5$ is C1-10 alkyl, phenyl, or benzyl.

16. The intermediate I according to claim 1, wherein $R_5$ is methyl, ethyl, isopropyl, tert-butyl, benzhydryl, benzyl, p-nitrobenzyl, p-methoxybenzyl, 4-pyridylbenzyl, trichloroethyl, methylthioethyl, p-toluenesulfonyl ethyl, p-nitrophenylthioethyl, phenyl, or benzyl.

17. The intermediate I according to claim 2, wherein $R_5$ is methyl, ethyl, isopropyl, tert-butyl, benzhydryl, benzyl, p-nitrobenzyl, p-methoxybenzyl, 4-pyridylbenzyl, trichloroethyl, methylthioethyl, p-toluenesulfonyl ethyl, p-nitrophenylthioethyl, phenyl, or benzyl.

18. The intermediate I according to claim 1, wherein the intermediate I is selected from the following compounds:
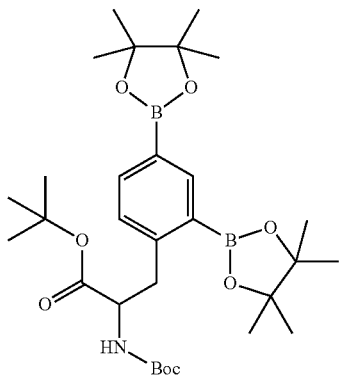
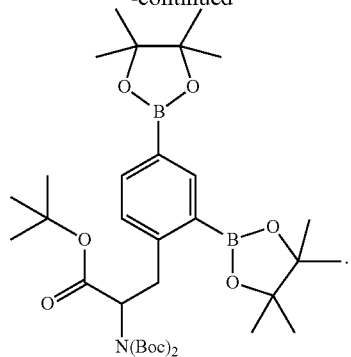
19. The intermediate I according to claim 5, wherein the substituent that is hydrolyzable to a boric acid group is a boric acid pinacol ester group.
20. The intermediate I according to claim 5, wherein $R_5$ is tert-butyl.
* * * * *